US008892211B2

(12) United States Patent
Grill et al.

(10) Patent No.: US 8,892,211 B2
(45) Date of Patent: Nov. 18, 2014

(54) SYSTEM AND METHOD FOR SELECTIVE RETINAL STIMULATION

(75) Inventors: Warren M. Grill, Cleveland Heights, OH (US); Matthew A. Schiefer, University Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 522 days.

(21) Appl. No.: 12/789,063

(22) Filed: May 27, 2010

(65) Prior Publication Data
US 2010/0305659 A1    Dec. 2, 2010

Related U.S. Application Data

(63) Continuation of application No. 11/735,417, filed on Apr. 13, 2007, now abandoned.

(60) Provisional application No. 60/744,749, filed on Apr. 13, 2006.

(51) Int. Cl.
*A61N 1/05* (2006.01)
*A61N 1/36* (2006.01)

(52) U.S. Cl.
CPC .......... *A61N 1/36046* (2013.01); *A61N 1/0543* (2013.01)
USPC .............................. 607/53; 607/54; 607/141

(58) Field of Classification Search
CPC ................... A61N 1/36046; A61N 1/0543
USPC ............................................. 607/53, 54, 141
See application file for complete search history.

(56) References Cited

U.S. PATENT DOCUMENTS

| 6,458,157 B1 | 10/2002 | Suaning |
| 6,560,490 B2 | 5/2003 | Grill et al. |
| 2002/0123780 A1* | 9/2002 | Grill et al. .................. 607/72 |
| 2005/0070973 A1* | 3/2005 | Tashiro et al. ............... 607/54 |
| 2007/0142877 A1 | 6/2007 | McLean |

OTHER PUBLICATIONS

Carras, et al., "Site of Action Potential Initiation in Amphibian Retinal Ganglion Cells", Journal of Neurophysiology, vol. 67, No. 2, Feb. 1992, pp. 292-304.
Greenberg et al., "A Computational Model of Electric Stimulation of the Retinal Ganglion Cell", IEEE Transactions on Biomedical Engineering, vol. 46, No. 5, May 1999, pp. 505-514.
Humayun, et al., "Pattern Electrical Stimulation of the Human Retina", Vision Research 39 (1999), 2569-2576.

(Continued)

*Primary Examiner* — Tammie K Heller
(74) *Attorney, Agent, or Firm* — Tarolli, Sundheim, Covell & Tummino LLP

(57) ABSTRACT

A method for electrically stimulating a retina of an eye to induce visual perception includes placing an electrode adjacent a retinal ganglion cell (RGC) layer and selectively applying a biphasic asymmetrical waveform (BAW) to a portion of the axon. The BAW includes a pre-pulse phase and a stimulation-pulse phase. The pre-pulse phase has a first polarity, a first amplitude, and a first duration. The first amplitude and the first duration together define a pre-pulse charge having a first magnitude. The stimulation-pulse phase has a second polarity opposite the first polarity, a second amplitude, and a second duration less than the first duration. The second amplitude and the second duration together define a stimulation charge having a second magnitude. Application of the pre-pulse phase and the stimulation-pulse phase effects a change in excitability of the at least one ganglion cell and induces visual perception, respectively.

13 Claims, 3 Drawing Sheets

(56) References Cited

OTHER PUBLICATIONS

McIntyre et al., "Selective Microstimulation of Central Nervous System Neurons", Annals of Biomedical Engineering, vol. 28, 2000, pp. 219-333.

Jenson et al., "Thresholds for Activation of Rabbit Retinal Ganglion Cells with an Ultrafine, Extracellular Microelectrode", Investigative Ophthalmology & Visual Science, Aug. 2003, vol. 44, No. 8, pp. 3533-3543.

Rizzo, III et al., "Perceptual Efficacy of Electrical Stimulation if Human Retina with a Microelectrode Array during Shirt-Term Trials", Investigative Ophthalmology & Visual Science, Dec. 2003, vol. 44, No. 12, pp. 5362-5369.

Schiefer et al., "Sites of Neuronal Excitation by Epiretinal Electrical Stimulation", IEEE Transactions on Neural Systems and Rehabilitation Engineering, vol. 14, No. 1, Mar. 2006, pp. 5-13.

Weiland et al., "Understanding the Origin of Visual Percepts Elicited by Electrical Stimulation of the Human Retina", Clinical Investigation, Graefe's Arch Clin Exp Ophthalmol (1999), pp. 1007-1003.

* cited by examiner

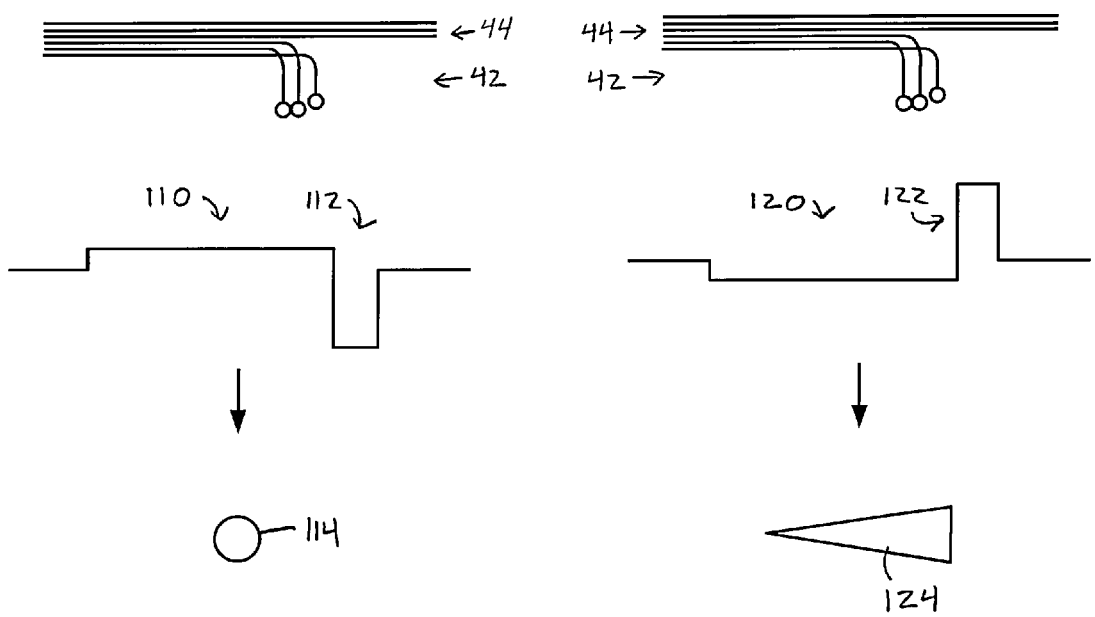
FIG. 5  FIG. 6

SYSTEM AND METHOD FOR SELECTIVE RETINAL STIMULATION

RELATED APPLICATIONS

This application is a Continuation of U.S. patent application Ser. No. 11/735,417, filed Apr. 13, 2007, (now abandoned), which claims priority from U.S. Provisional Application No. 60/744,749, filed Apr. 13, 2006 (Expired). The present application claims priority to the aforementioned patent applications, which are incorporated in their entirety herein by reference for all purposes.

FIELD OF THE INVENTION

The present invention relates generally to electrical stimulation of sensory nerves, and in particular electrical stimulation of retinal ganglion cells of an eye to induce visual perception.

BACKGROUND

In many patients who are blinded by degenerative conditions, the photoreceptors of the retina may no longer function normally. For many of these patients, however, the retinal ganglion cells can continue to function and provide a signal pathway through the central nervous system to the brain.

A typical eye 10 and the relative location of its components is schematically illustrated in FIGS. 1 and 2. The eye 10 is a generally circular globe filled with aqueous humour 12, a clear liquid that is similar to water. The eye 10 also includes 20 cornea 14, which is a transparent structure that admits light into the eye 10. The amount of light passing into the eye 10 is controlled by an iris 16, a muscle that moves to allow or block light from passing through a lens 20 behind the iris 16 to the interior of the eye 10. The lens 20 focuses light passing therethrough onto the retina 22. The retina 22 forms the interior surface of the eye opposite the lens. The output of the retina 22 is carried by retinal ganglion cells 30 that transmit action potentials to the brain via the optic nerve 24.

In the eye 10, the retina 22 is a multilayered tissue that includes a layer of rods 26 and cones 28 which are the photoreceptors that detect the light falling thereon and help to convert the image projected on the retina 22 into electrical signals that can be interpreted by the brain as sight. The rods 26 provide vision in dim light and do not respond to bright light. Cones 28 on the other hand, do not respond to dim light, but provide color and fine detail vision. An inner nuclear layer separates the rods 26 and cones 28 from the ganglion cells 30 and includes amacrine cells 32, bipolar cells 34 and horizontal cells 36.

A common structural feature of ganglion cells 30 is an approximately 90° bend 40 in the axon as the axon leaves the ganglion cell layer 42 and enters the nerve fiber layer 44. The axons of the retinal ganglion cells 30 pass across the surface of the retina 22 and collect before exiting to form the optic nerve 24. In a healthy eye, light detected by the rods 26 and cones 28 generate signals that are transmitted via the retinal ganglion cells 30 and the optic nerve 24 to the brain, which perceives the visual image.

SUMMARY

An exemplary method for electrically stimulating a retina of an eye to induce visual perception includes the following steps: placing an electrode adjacent a retinal ganglion cell layer; effecting a change in the excitability of cells in the ganglion cell layer by selectively applying a biphasic asymmetrical waveform having a relatively long duration and a relatively low amplitude pre-pulse phase of a first polarity, and inducing visual perception by selectively applying a biphasic asymmetrical waveform having a relatively short duration and relatively high amplitude stimulation pulse phase that follows the pre-pulse phase. The stimulation pulse phase has a second polarity opposite the first polarity of the pre-pulse phase. A cathodic pre-pulse phase and an anodic stimulation phase induce the perception of a circular (punctuate) shape, and an anodic pre-pulse phase and a cathodic stimulation phase induce the perception of an elongated (streak) shape.

The pre-pulse phase has a magnitude that is below a threshold value at which ganglion nerve cells are activated to pass a signal (sub-threshold magnitude), and has a duration that is sufficient to increase the excitability of the selected type of ganglion nerve cell. An anodic pre-pulse phase applied at a sub-threshold magnitude and for a duration that is sufficient to increase the excitability of a bending region of an axon helps to induce the perception of a circular shape in response to the stimulation phase. Applying a cathodic pre-pulse phase at a sub-threshold magnitude and for a duration sufficient to increase the excitability of the passing region of an axon helps to induce the perception of an elongated shape in response to the stimulation phase. Typically, the stimulation pulse phase has a suprathreshold magnitude that balances the charge injected by the pre-pulse phase. The pre-pulse phase typically lasts for no more than about one millisecond. The duration of the stimulation pulse phase to the duration of the pre-pulse phase is approximately 10:1.

Another method includes the steps of placing an electrode adjacent a retinal ganglion cell layer and effecting a change in the excitability of cells in the ganglion cell layer by selectively applying a biphasic asymmetrical waveform. The waveform has a pre-pulse phase having a first polarity, a first amplitude and a first duration. The first amplitude and first duration together define a pre-pulse charge having a first magnitude and the first polarity. The waveform also includes a stimulation-pulse phase following the pre-pulse phase, the stimulation-pulse phase having a second polarity opposite the first polarity, a second amplitude and second duration less than the first duration. The second amplitude and second duration together define a stimulation charge having the second polarity and a second magnitude that equals the first magnitude.

A visual neuroprosthesis for electrically stimulating a retina of an eye to induce visual perception generally includes an electrode positionable near a ganglion cell layer of the retina of an eye, and a waveform generator capable of generating a waveform for selectively stimulating either bending axons to induce the perception of a circular image or passing axons to induce the perception of a streak image.

U.S. Pat. No. 6,560,490, which includes work performed by an inventor of the present invention in the field of central nervous system (CNS) stimulation, is hereby incorporated herein by reference. In contrast to this earlier patent, the present application recognizes the applicability of electrical stimulation to the eye and applies a biphasic asymmetrical waveform to produce selectively different types of perception, i.e., either spots or streaks, based on the polarity, duration and magnitude of the pre-pulse phase and the stimulation phase.

The foregoing and other features of the invention are shown in the drawings and particularly pointed out in the claims. The following description and annexed drawings set forth detail one or more illustrated embodiments of the inven-

BRIEF DESCRIPTION OF THE DRAWINGS

FIGS. 5 and 6 are schematic illustrations of biphasic asymmetrical waveforms and the resulting visual perception induced thereby.

DETAILED DESCRIPTION

Figure 3:
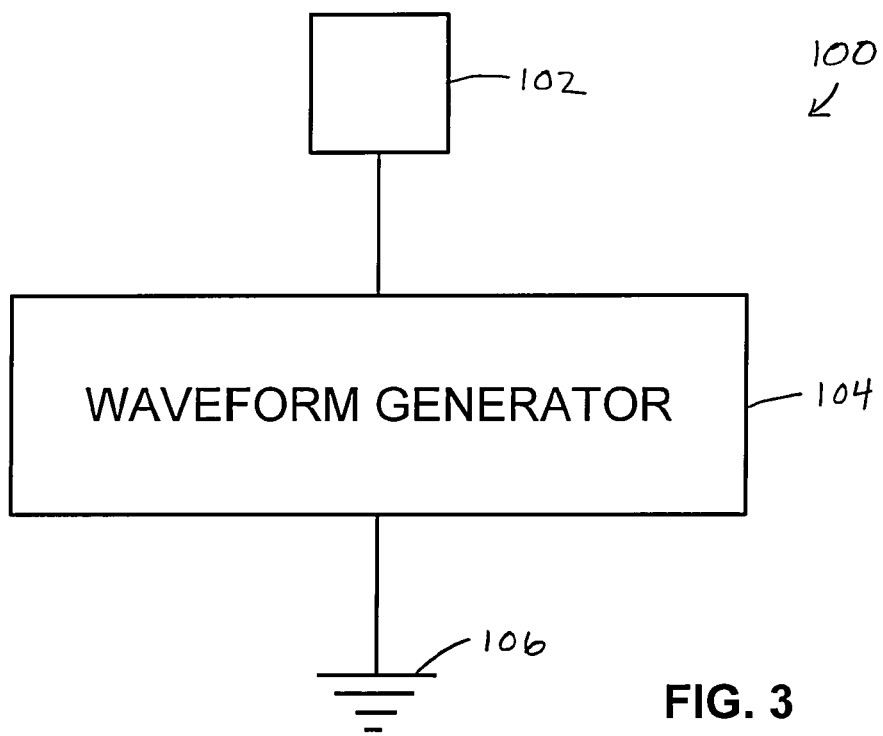
FIG. 3 is a schematic drawing of a neuroprosthesis that can be used in accordance with the present invention.
Figure 1:
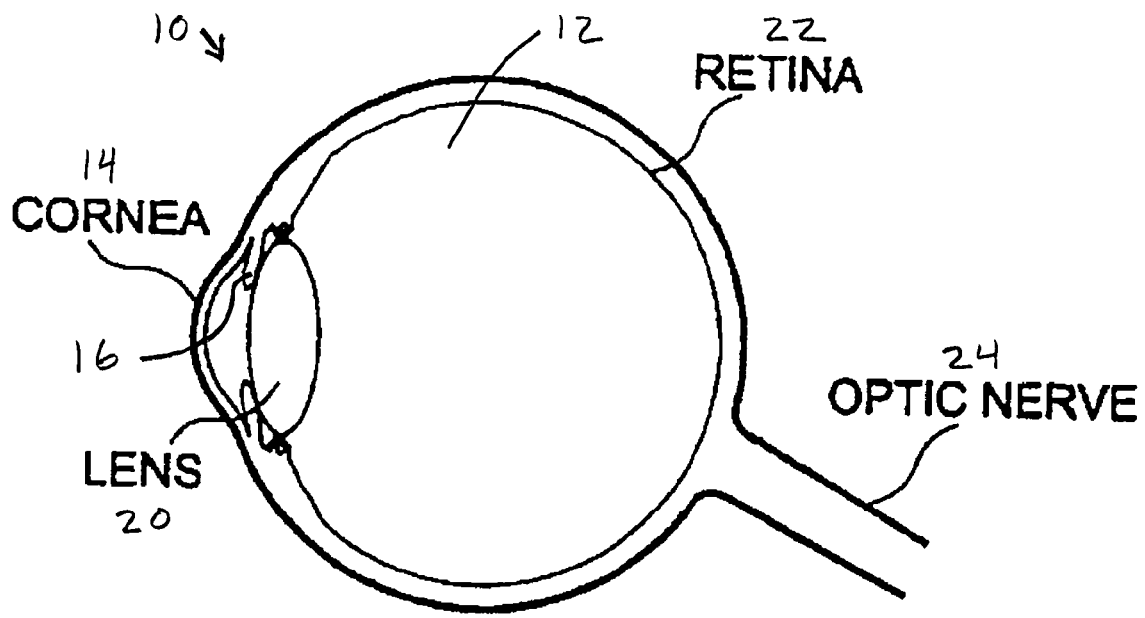
FIG. 1 is a schematic cross-sectional view of an eye.
Figure 2:
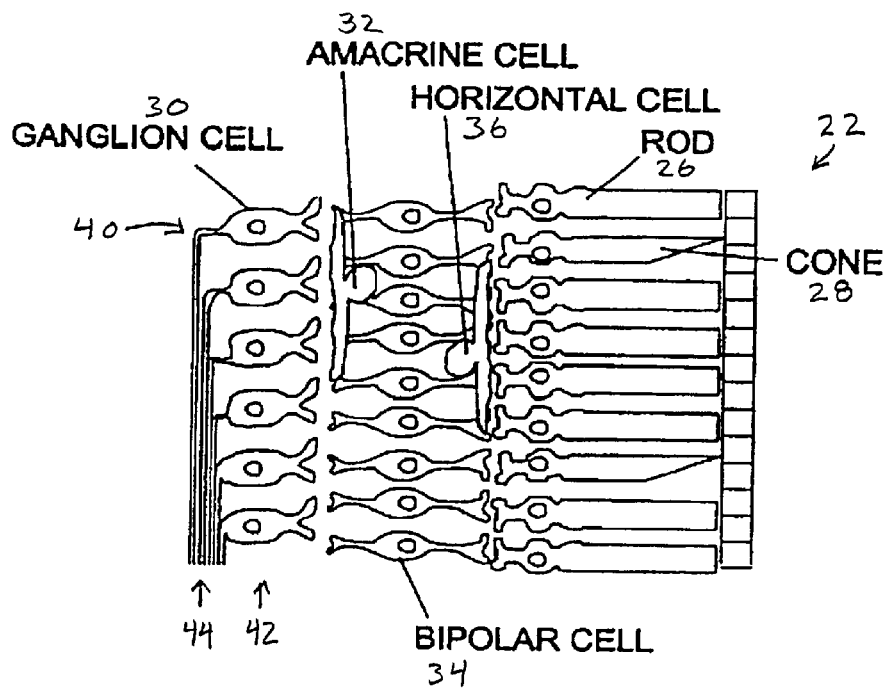
FIG. 2 is an enlarged schematic view of a portion of a retina portion of the eye.
Figure 4:
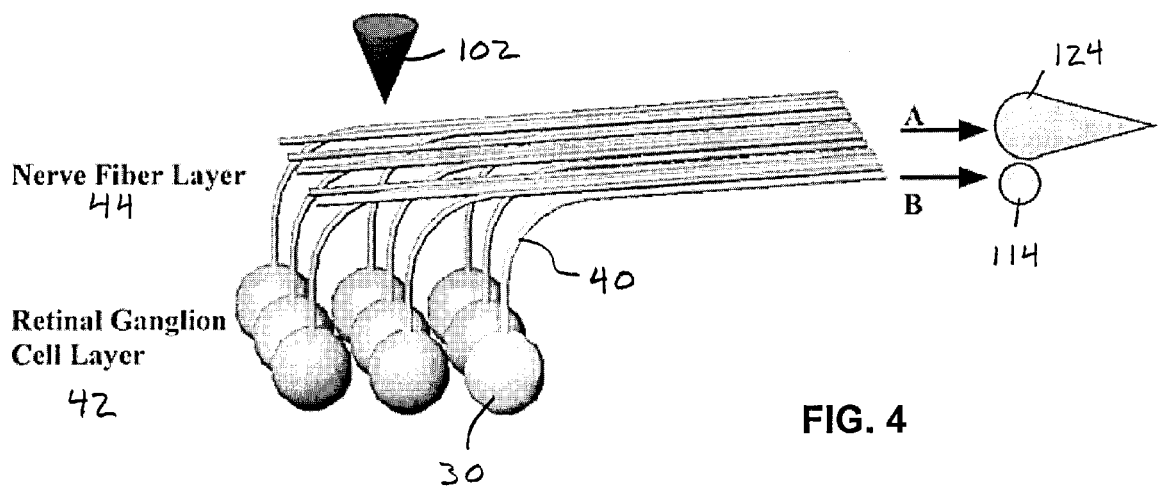
FIG. 4 is a schematic representation of an electrode and retinal ganglion cells.

Referring now to the drawings in detail, and initially to FIGS. 1-4, a visual neuroprosthesis 100 for electrically stimulating a retina 22 of an eye 10 to induce visual perception includes an electrode 102 that can be positioned near a ganglion cell layer 40 of a retina 22, and a waveform generator 104 connected to the electrode 102. The threshold for excitation of a retinal ganglion cell 30 with an epiretinal electrode generally is lower when the electrode is located in proximity to the characteristic 90° bend (bending region) 40 in the axon of the ganglion cell 30 than when it is located over a passing axon of the nerve fiber layer 44. The waveform generator 104 is capable of generating a waveform in the electrode 102 for selectively stimulating either bending axons 40 of the retinal ganglion cell layer 42 to induce the perception of a circular image (punctuate, spot) or passing axons of the nerve fiber layer 44 to induce the perception of an elongate image (pie, streak, teardrop).

The waveform generator 104 is configured or programmed to output biphasic, asymmetric waveforms to induce the desired visual perception. The waveform generator 104 also may have a ground or reference potential 106, and may be implanted into a body or remotely located outside the body. The hardware of such a generator is conventional. Likewise, the electrode 102 may be a conventional electrode, such as a metal microelectrode or a multiple-contact electrode that can be placed adjacent the eye, including on the eye.

A method for electrically stimulating a retina of an eye, using the aforementioned waveform generator 104 and electrode 102, for example, may be performed to selectively induce visual perception of either an elongate image (sometimes referred to as a streak phosphene) or a spot image (sometimes referred to as a punctuate phosphene). The method includes the steps of placing an electrode 102 adjacent an eye, particularly near a retinal ganglion cell layer 42, and effecting a change in the excitability of the cells 30 in the ganglion cell layer 42 or the nerve fiber layer 44. After effecting the change in the excitability, the method includes inducing visual perception.

The effecting and inducing steps are performed by selectively applying a biphasic asymmetrical waveform. The waveform has a relatively long duration and relatively low amplitude (sub-threshold) pre-pulse phase of a first polarity, and a relatively short duration and relatively high amplitude (supra-threshold) stimulation pulse phase of a second polarity opposite the first polarity. Further, an interphase delay may be introduced between the delivery of the pre-pulse phase and stimulation phase of the waveform. To preserve charge-balancing, the charge delivered by the pre-pulse phase is equal in magnitude and opposite in polarity relative to the charge delivered by the stimulation pulse phase.

As shown in FIG. 5, a cathodic (positive) pre-pulse phase 110 and an anodic (negative) stimulation phase 112 following the pre-pulse phase 110 have been found to increase the excitation of a passing region of an axon in a nerve fiber layer 44 and to induce the perception of a circular or spot shape 114. The same pre-pulse phase 110 of the waveform that increases the susceptibility of the passing region of the axon to stimulation decreases the susceptibility of a bending region 40 of an axon to 5 excitation by the subsequent stimulation pulse phase 112 of the waveform. The opposite also applies when applying an anodic pre-pulse phase followed by a cathodic stimulation phase.

Referring now to FIG. 6, an anodic pre-pulse phase 120 and a cathodic stimulation phase 122 increase the excitation of a bending region 40 of an axon and induce the perception of an elongate or streak shape 124.

The threshold for ganglion cell stimulation is the point at which the electrical pulse generates propagating action potentials in the axon. The stimulation threshold generally is lower when the electrode 102 is located in proximity to the characteristic ninety degree bend 40 in the axon than when it is located over a passing axon of the nerve fiber layer 44. The stimulation pulse phase typically has a magnitude that balances the charge injected by the pre-pulse phase, and generally has a duration of no more than about one millisecond. The pulse width typically is about fifty microseconds to about five hundred microseconds. And the duration of the pre-pulse phase to the duration of the stimulation-pulse phase is approximately 10:1.

This approach may be applied across multiple electrodes, which may be contained within an electrode array, to produce multiple phosphenes (spots and streaks) and the perception of an image. Different waveforms (polarity, duration, intensity) would be delivered selectively to different electrodes within the array to produce the desired set of phosphenes and thereby the desired image.

Exemplary stimulus waveforms are shown and described in U.S. Pat. No. 6,560,490, which is incorporated herein by reference. In addition to the aforementioned patent, C. C. Mcintyre and W. M. Grill, "Selective Microstimulation of Central Nervous System Neurons," Annals of Biomedical Engineering, vol. 28, pp. 219-233, 2000, is hereby incorporated herein by reference.

Although the invention has been shown and described with respect to certain preferred embodiments, equivalent alterations and modifications will occur to others skilled in the art upon reading and understanding the specification and the annexed drawings. In particular regard to the various functions performed by the above described integers (components, assemblies, devices, compositions, etc.), the terms (including a reference to "means") used to describe such integers are intended to correspond, unless otherwise indicated, to any integer which performs the specified function of the described integer (i.e. that is functionally equivalent), even though not structurally equivalent to the disclosed structure which performs the function in the herein illustrated exemplary embodiment or embodiments of the invention. In addition, while a particular feature of the invention may have been described above with respect to only one of several illustrated embodiments, such feature can be combined with one or more other features of the other embodiments, as may be desired and advantageous for any given or particular application.

What is claimed is:

1. A method for electrically stimulating a retina of an eye to induce visual perception, said method comprising the steps of:
   placing an electrode within the eye in proximity to a retinal ganglion cell (RGC) layer; and
   applying a biphasic, asymmetrical, charge-balanced waveform to at least a portion of the RGC layer,
   said biphasic, asymmetrical, charge-balanced waveform comprising:
   a pre-pulse phase having a first polarity, a sub-threshold first amplitude, and a first duration to change the excitability of at least one cell related to the at least the portion of the RGC layer; and
   a stimulation-pulse phase following the pre-pulse phase having a second polarity opposite the first polarity, a supra-threshold second amplitude, and a second duration less than the first duration to induce visual perception.

2. The method of claim 1, wherein said stimulation-pulse phase follows said pre-pulse phase.

3. The method of claim 1, wherein the first polarity is a cathodic polarity and the second polarity is an anodic polarity to induce visual perception of a circular shape.

4. The method of claim 3, wherein the first duration is of a duration sufficient to increase excitability of a passing region of an axon in a nerve fiber layer adjacent to the portion of the RGC layer.

5. The method of claim 1, wherein the first polarity is an anodic polarity and the second polarity is a cathodic polarity to induce perception of an elongated shape.

6. The method of claim 5, wherein the first duration is sufficient to increase excitability of an approximately 90° bending region of the at least one cell.

7. The method of claim 1, wherein said step of placing an electrode within the eye adjacent a RGC layer further includes placing said electrode within the eye adjacent an approximately 90° bending region of the RGC layer.

8. The method of claim 1, wherein a charge delivered by said stimulation-pulse phase balances a charge delivered by said pre-pulse phase.

9. The method of claim 1, wherein said first duration of said pre-pulse phase is approximately ten times longer than said second duration of said stimulation-pulse phase.

10. The method of claim 1, wherein said biphasic, asymmetrical, charge-balanced waveform further comprises an interphase delay between said pre-pulse phase and said stimulation-pulse phase.

11. A method for electrically stimulating a retina of an eye to induce visual perception, said method comprising the steps of:
   placing an electrode within the eye in proximity to a retinal ganglion cell (RGC) layer; and
   selecting a first polarity and a second polarity of a biphasic, asymmetrical, charge balanced waveform, wherein the second polarity is opposite to the first polarity, wherein the first polarity and the second polarity are selected to induce a visual perception;
   applying the biphasic, asymmetrical, charge balanced waveform to at least a portion of the RGC layer,
   said biphasic, asymmetrical, charge-balanced waveform comprising:
   a pre-pulse phase comprising the first polarity, a sub-threshold first amplitude, and a first duration to change the excitability of at least one cell related to the at least the portion of the RGC layer; and
   a stimulation-pulse phase comprising the second polarity, a supra-threshold second amplitude, and a second duration less than the first duration to induce the visual perception.

12. The method of claim 11, wherein the first polarity is cathodic, the second polarity is anodic, and the visual perception comprises the perception of a circular shape; or
   wherein the first polarity is anodic, the second polarity is cathodic, and the visual perception comprises the perception of an elongated shape.

13. A method for electrically stimulating a retina of an eye to induce visual perception, said method comprising the steps of:
   placing an electrode within the eye in proximity to a retinal ganglion cell (RGC) layer; and
   selecting parameters to balance the charge of a biphasic, asymmetrical waveform, wherein the parameters include:
   first parameters of a pre-pulse phase comprising a first polarity, a sub-threshold first amplitude, and a first duration, and
   second parameters of a stimulation-pulse phase comprising a second polarity opposite to the first polarity, a supra-threshold second amplitude, and a second duration at least ten times shorter than the first duration;
   applying the biphasic, asymmetrical waveform with the charge balanced according to the selected parameters to at least a portion of the RGC layer,
   said biphasic, asymmetrical waveform comprising:
   the pre-pulse phase comprising the first polarity, the sub-threshold first amplitude, and the first duration to change the excitability of at least one cell related to the at least the portion of the RGC layer; and
   the stimulation-pulse phase comprising the second polarity, the supra-threshold second amplitude, and the second duration to induce the visual perception;
   wherein the first polarity is cathodic, the second polarity is anodic, and the visual perception induced is of a circular shape; or
   wherein the first polarity is anodic, the second polarity is cathodic, and the visual perception induced is of an elongated shape.

* * * * *